United States Patent
Yacyshyn et al.

(10) Patent No.: US 11,085,912 B2
(45) Date of Patent: Aug. 10, 2021

(54) **METHODS OF DIAGNOSING *CLOSTRIDIUM DIFFICILE* INFECTION OR RECURRENCE IN A SUBJECT**

(71) Applicant: University of Cincinnati, Cincinnati, OH (US)

(72) Inventors: Mary Elizabeth Yacyshyn, Cincinnati, OH (US); Bruce R. Yacyshyn, Cincinnati, OH (US); Julianne Qualtieri, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 15/841,453

(22) Filed: Dec. 14, 2017

(65) Prior Publication Data

US 2018/0164282 A1   Jun. 14, 2018

Related U.S. Application Data

(60) Provisional application No. 62/433,870, filed on Dec. 14, 2016.

(51) Int. Cl.
| | |
|---|---|
| *G01N 33/49* | (2006.01) |
| *G01N 21/47* | (2006.01) |
| *G01N 33/569* | (2006.01) |
| *G01N 33/68* | (2006.01) |
| *G01N 33/574* | (2006.01) |
| *C12Q 1/04* | (2006.01) |
| *G01N 15/14* | (2006.01) |
| *G01N 15/12* | (2006.01) |
| *G01N 15/10* | (2006.01) |

(52) U.S. Cl.
CPC ............. *G01N 33/491* (2013.01); *C12Q 1/04* (2013.01); *G01N 15/12* (2013.01); *G01N 15/1434* (2013.01); *G01N 15/1459* (2013.01); *G01N 21/47* (2013.01); *G01N 33/569* (2013.01); *G01N 33/56972* (2013.01); *G01N 33/574* (2013.01); *G01N 33/6893* (2013.01); *G01N 2015/1006* (2013.01); *G01N 2333/7051* (2013.01); *G01N 2333/70503* (2013.01); *G01N 2333/70514* (2013.01); *G01N 2333/70517* (2013.01); *G01N 2333/70535* (2013.01); *G01N 2800/26* (2013.01); *G01N 2800/50* (2013.01); *G01N 2800/54* (2013.01)

(58) Field of Classification Search
CPC ................. G01N 33/491; G01N 21/47; G01N 33/56972; G01N 2800/26; G01N 2800/50; G01N 2333/70503; G01N 2333/70514; G01N 2333/70517; G01N 2333/7051; G01N 2333/70535; G01N 2800/54

See application file for complete search history.

(56) References Cited

U.S. PATENT DOCUMENTS

| | | | |
|---|---|---|---|
| 2010/0035235 A1 | 2/2010 | Gabriel | |
| 2012/0149592 A1* | 6/2012 | Love | G01N 33/5047 506/9 |
| 2014/0212879 A1* | 7/2014 | Kubota | C12Q 1/689 435/6.11 |

OTHER PUBLICATIONS

Kelly et al. Current Concepts—Clostridium difficile colitis. The New England Journal of Medicine (1994), v330(4), p. 257-262. (Year: 1994).*
Modi et al. Differential Binding and Internalization of Clostridium difficile Toxin A by Human Peripheral Blood Monocytes, Neutrophils and Lymphocytes. Scandanavian Journal of Immunology (2011), v74, p. 264-271. (Year: 2011).*
Dean L. Blood Groups and Red Cell Antigens [Internet], Bethesda (MD): National Center for Biotechnology Information (US); 2005. Chapter 1, Blood and the cells it contains. Available from: https://www.ncbi.nlm.nih.gov/books/NBK2263/ (Year: 2005).*
Stewart et al. Resolving Leukocytes Using Axial Light Loss. Cytometry (1989), v10, p. 426-432. (Year: 1989).*
Steen et al. Simultaneous Separate Detection of Low Angle and Large Angle Light Scattering in an Arc Lamp-Based Flow Cytometer. Cytometry (1986), v7, p. 445-449 (Year: 1986).*
Gille-Johnson et al. Clinical and laboratory variables identifying bacterial infection and bacteraemia in the emergency department. Scand J Infect Dis (2012), 44(10), 745-752, Abstract Only. (Year: 2012).*
Tefferi et al. How to Interpret and Pursue an Abnormal Complete Blood Cell Count in Adults. Mayo Clin Proc (2005), 80(7), 923-936. (Year: 2005).*
Bulusu et al. Leukocytosis as a Harbinger and SurrogateMarker of Clostridium difficile Infection in Hospitalized Patients With Diarrhea. Am J Gasteroenterol (2000), 95(11), 3137-3141. (Year: 2000).*

(Continued)

*Primary Examiner* — Sean C. Barron
(74) *Attorney, Agent, or Firm* — Wood Herron & Evans LLP

(57) ABSTRACT

Methods are described for identifying CDI patients as well as CDI patients at risk for recurrence. Embodiments include: (1) flow cytometry of circulating peripheral blood mononuclear cells (PBMC) to phenotype for the less efficient immunoglobulin response to bacterial toxins and surface antigens that characterizes patients who will become recurrent; (2) stratification by means of complete blood count (CBC) using a Coulter counter to detect the differences in lower angle light scatter (LAL), which has a larger range in the recurrent population; and (3) stratification by means of complete blood count (CBC) using a Coulter counter to detect the lower axial light loss (AL2) exhibited in recurrent patients.

2 Claims, 20 Drawing Sheets

(56) References Cited

OTHER PUBLICATIONS

M.D. Graham. The Coulter Principle: Foundation of an Industry. JALA (2003), 8, 72-81. (Year: 2003).*

"Plurality" (2014). In Collins Dictionaries (Ed.), Collins English Dictionary (12th ed.). Collins. Credo Reference: https://search.credoreference.com/content/entry/hcengdict/plurality/0?institutionId=743; (Year: 2014).*

Yacyshyn MB, et al., Clostridium difficile recurrence is characterized by pro-inflammatory peripheral blood mononuclear cell (PBMC) phenotype, Jounral of Medical Microbiology (2014) 63, 1260-1273.

* cited by examiner two (neutrophils and lymphocytes)

```
Descriptive Statistics
                Ca2AL2         In2AL2         Re2AL2
N                   39             40             22
Missing              1              0             18
Sum               9070           9786           5398
Lo 95% CI       227.96         239.48         234.81
Mean            232.56         244.65         245.36
Up 95% CI       237.16         249.82         255.92
SD              14.190         16.152         23.800
Variance        201.36         260.90         566.43
SE Mean         2.2722         2.5539         5.0741
C.V.            6.1016         6.6022         9.6998
Minimum         207.00         211.00         211.00
1st Quarti      223.00         231.50         223.00
Median          235.00         247.00         245.00
3rd Quarti      242.00         258.00         259.25
Maximum         273.00         268.00         307.00
MAD             10.000         11.500         14.500
Biased Var      196.19         254.38         540.69
Skew            0.3718        -0.3356         0.5988
Kurtosis        0.2840        -0.9339         0.1751

Kruskal-Wallis One-Way Nonparametric AOV

Mean    Sample
Variable    Rank    Size
Ca2AL2      38.8      39
In2AL2      59.7      40
Re2AL2      56.8      22
Total       51.0     101

Kruskal-Wallis Statistic                          11.1325
P-Value, Using Chi-Squared Approximation           0.0038

Parametric AOV Applied to Ranks
Source      DF       SS          MS        F         P
Between      2    9548.9     4774.47     6.14    0.0031
Within      98   76226.6      777.82
Total      100   85775.5

Total number of values that were tied    83
Max. diff. allowed between ties     0.00001

Cases Included 101    Missing Cases 19
```

FIG. 2

```
Wilcoxon Rank Sum Test for Ca2AL2 VS In2AL2
Variable     Rank Sum      N      U Stat   Mean Rank
Ca2AL2         1221.5     39      441.50     31.3
In2AL2         1938.5     40     1118.5      48.5
Total          3160.0     79

Normal Approximation with Corrections for Continuity and Ties    3.316
Two-tailed P-value for Normal Approximation                      0.0009

Total number of values that were tied          61
Maximum difference allowed between ties 0.00001

Cases Included 79    Missing Cases 1

Statistix 9.1
Wilcoxon Rank Sum Test for Ca2AL2 VS Re2AL2

Variable     Rank Sum      N      U Stat   Mean Rank
Ca2AL2         1072.5     39      292.50     27.5
Re2AL2          818.50    22      565.50     37.2
Total          1891.0     61

Normal Approximation with Corrections for Continuity and Ties    2.044
Two-tailed P-value for Normal Approximation                      0.0410

Total number of values that were tied          44
Maximum difference allowed between ties 0.00001

Cases Included 61    Missing Cases 19
```

FIG. 4

```
Descriptive Statistics
                      CasAL2        IniAL2        RecAL2
 N                        39            40            22
 Missing                   1             0            18
 Sum                   14663         15823          8639
 Lo 95% CI            368.06        386.64        374.66
 Mean                 375.97        395.57        392.68
 Up 95% CI            383.88        404.51        410.71
 SD                   24.401        27.931        40.651
 Variance             595.39        780.15        1652.5
 SE Mean              3.9072        4.4163        8.6668
 C.V.                 6.4900        7.0609        10.352
 Minimum              326.00        338.00        328.00
 1st Quarti           361.00        376.75        354.75
 Median               377.00        403.00        396.50
 3rd Quarti           390.00        416.00        428.25
 Maximum              432.00        444.00        490.00
 MAD                  14.000        17.000        32.000
 Biased Var           580.13        760.64        1577.4
 Skew                 0.1279       -0.3591        0.3336
 Kurtosis            -0.2088       -0.8174       -0.3051

Kruskal-Wallis One-Way Nonparametric AOV

Mean    Sample
Variable   Rank    Size
IniAL2     59.9      40
CasAL2     39.8      39
RecAL2     54.6      22
Total      51.0     101

Kruskal-Wallis Statistic                        9.7288
P-Value, Using Chi-Squared Approximation        0.0077

Parametric AOV Applied to Ranks
Source     DF       SS         MS         F         P
Between     2    8349.5    4174.76      5.28    0.0066
Within     98   77473.0     790.54
Total     100   85822.5

Total number of values that were tied   58
Max. diff. allowed between ties       0.00001

Cases Included 101    Missing Cases 19
```

FIG. 5

```
Wilcoxon Rank Sum Test for CasAL2 VS IniAL2

Variable    Rank Sum      N      U Stat   Mean Rank
CasAL2       1234.0       39     454.00      31.6
IniAL2       1926.0       40     1106.0      48.2
Total        3160.0       79

Normal Approximation with Corrections for Continuity and Ties   3.192
Two-tailed P-value for Normal Approximation                     0.0014

Total number of values that were tied         42
Maximum difference allowed between ties 0.00001

Cases Included 79    Missing Cases 1

Variable    Rank Sum      N      U Stat   Mean Rank
CasAL2       1099.0       39     319.00      28.2
RecAL2       792.00       22     539.00      36.0
Total        1891.0       61

Normal Approximation with Corrections for Continuity and Ties   1.645
Two-tailed P-value for Normal Approximation                     0.0999

Total number of values that were tied         23
Maximum difference allowed between ties 0.00001

Cases Included 61    Missing Cases 19
Wilcoxon Rank Sum Test for RecAL2 VS IniAL2

Variable    Rank Sum      N      U Stat   Mean Rank
RecAL2       661.50       22     408.50      30.1
IniAL2       1291.5       40     471.50      32.3
Total        1953.0       62

Normal Approximation with Corrections for Continuity and Ties   0.456
Two-tailed P-value for Normal Approximation                     0.6482

Total number of values that were tied         25
Maximum difference allowed between ties 0.00001

Cases Included 62    Missing Cases 18
```

FIG. 7

```
Descriptive Statistics
                CDI-         CDI +
N                 39             62
Missing           23              0
Sum            14663          24462
Lo 95% CI     368.06         386.24
Mean          375.97         394.55
Up 95% CI     383.88         402.85
SD            24.401         32.705
Variance      595.39         1069.6
SE Mean       3.9072         4.1536
C.V.          6.4900         8.2893
Minimum       326.00         328.00
1st Quarti    361.00         369.50
Median        377.00         399.00
3rd Quarti    390.00         416.00
Maximum       432.00         490.00
MAD           14.000         21.000
Biased Var    580.13         1052.4
```

FIG. 8

```
Descriptive Statistics

CDI-        CDI+
N                 39          62
Missing           23           0
Sum             9070       15184
Lo 95% CI     227.96      240.07
Mean          232.56      244.90
Up 95% CI     237.16      249.73
SD            14.190      19.024s
Variance      201.36      361.92
SE Mean       2.2722      2.4161
C.V.          6.1016      7.7681
Minimum       207.00      211.00
1st Quarti    223.00      230.75
Median        235.00      247.00
3rd Quarti    242.00      259.00
Maximum       273.00      307.00
MAD           10.000      13.000
Biased Var    196.19      356.09
Skew          0.3718      0.2877
Kurtosis      0.2840      0.3261

Kruskal-Wallis One-Way Nonparametric AOV
            Mean    Sample
Variable    Rank     Size
CDI-        38.8      39
CDI+        58.7      62
Total       51.0     101

Kruskal-Wallis Statistic                      10.9873
P-Value, Using Chi-Squared Approximation       0.0009

Parametric AOV Applied to Ranks
Source      DF       SS        MS        F        P
Between      1     9424.4    9424.37   12.22    0.0007
Within      99    76351.1     771.22
Total      100    85775.5

Total number of values that were tied    83
Max. diff. allowed between ties    0.00001

Cases Included 101    Missing Cases 23
Wilcoxon Rank Sum Test for Ca2AL2 VS In2AL2

Variable    Rank Sum     N    U Stat    Mean Rank
CDI-         1514.0     39    734.00      38.8
CDI+         3637.0     62   1684.0       58.7
Total        5151.0    101

Normal Approximation with Corrections for Continuity and Ties    3.311
Two-tailed P-value for Normal Approximation                      0.0009

Total number of values that were tied         83
Maximum difference allowed between ties  0.00001
Cases Included 101    Missing Cases 23
```

FIG. 10

```
Descriptive Stats
                    Case2           Ini2            Rec2
N                      39             40              22
Missing                 1              0              18
Sum                  9475           9508            4751
Lo 95% CI          232.17         226.91          201.23
Mean               242.95         237.70          215.95
Up 95% CI          253.73         248.49          230.68
SD                 33.260         33.748          33.204
Variance           1106.3         1138.9          1102.5
SE Mean            5.3259         5.3360          7.0792
C.V.               13.690         14.198          15.376
Minimum            145.00         157.00          155.00
1st Quarti         229.00         225.50          186.75
Median             249.00         245.00          223.00
3rd Quarti         266.00         255.75          235.25
Maximum            290.00         300.00          271.00
MAD                17.000         13.500          16.500
Biased Var         1077.9         1110.5          1052.4
Skew              -1.2410        -0.6020         -0.1243
Kurtosis           1.4435         0.2297         -0.7579

Kruskal-Wallis One-Way Nonparametric AOV
              Mean    Sample
Variable      Rank    Size
Case2         59.1      39
Ini2          52.9      40
Rec2          33.3      22
Total         51.0     101

Kruskal-Wallis Statistic                          11.1235
P-Value, Using Chi-Squared Approximation          0.0038

Parametric AOV Applied to Ranks
Source       DF        SS          MS         F         P
Between       2      9547.0     4773.48     6.13     0.0031
Within       98     76280.0      778.37
Total       100     85827.0

Total number of values that were tied    51
Max. diff. allowed between ties       0.00001
```

FIG. 12

```
Wilcoxon Rank Sum Test for Case2 VS Rec2
Variable      Rank Sum      N      U Stat   Mean Rank
Case2          1421.0       39     641.00      36.4
Rec2           470.00       22     217.00      21.4
Total          1891.0       61

Normal Approximation with Corrections for Continuity and Ties    3.177
Two-tailed P-value for Normal Approximation                     0.0015
Total number of values that were tied           28
Maximum difference allowed between ties 0.00001

Cases Included 61    Missing Cases 19

Statistix 9.1                                        5/17/2015, 2:23:32 PM
Wilcoxon Rank Sum Test for Rec2 VS Ini2
Variable      Rank Sum      N      U Stat   Mean Rank
Rec2           516.00       22     263.00      23.5
Ini2           1437.0       40     617.00      35.9
Total          1953.0       62

Normal Approximation with Corrections for Continuity and Ties    2.597
Two-tailed P-value for Normal Approximation                     0.0094

Total number of values that were tied           18
Maximum difference allowed between ties 0.00001

Cases Included 62    Missing Cases 18
```

FIG. 14

```
Descriptive Statistics
                Case3          Ini3           Rec3
N                  38            38             21
Missing             0             0             17
Sum             15261         15369           7706
Lo 95% CI      387.52        391.24         348.73
Mean           401.61        404.45         366.95
Up 95% CI      415.69        417.66         385.18
SD             42.863        40.193         40.039
Variance       1837.2        1615.5         1603.1
SE Mean        6.9533        6.5202         8.7373
C.V.           10.673        9.9378         10.911
Minimum        258.00        313.00         292.00
1st Quarti     386.50        391.00         353.50
Median         410.50        409.00         372.00
3rd Quarti     429.75        426.50         390.50
Maximum        456.00        502.00         440.00
MAD            20.000        17.000         17.000
Biased Var     1788.9        1573.0         1526.8
Skew          -1.5261       -0.2959        -0.3064
Kurtosis       2.4323        0.4612        -0.1350

Kruskal-Wallis One-Way Nonparametric AOV

Mean    Sample
Variable     Rank     Size
Case3        54.9      38
Ini3         54.5      38
Rec3         28.4      21
Total        49.0      97

Kruskal-Wallis Statistic                        14.3942
P-Value, Using Chi-Squared Approximation         0.0007

Parametric AOV Applied to Ranks
Source      DF       SS         MS          F         P
Between      2    11399.3    5699.64      8.29    0.0005
Within      94    64626.2     687.51
Total       96    76025.5

Total number of values that were tied    43
Max. diff. allowed between ties       0.00001

Cases Included 97    Missing Cases 17
```

FIG. 15

```
Wilcoxon Rank Sum Test for Case3 VS Rec3

Variable    Rank Sum      N      U Stat    Mean Rank
Case3        1352.0       38     611.00       35.6
Rec3         418.00       21     187.00       19.9
Total        1770.0       59

Normal Approximation with Corrections for Continuity and Ties    3.349
Two-tailed P-value for Normal Approximation                      0.0008

Total number of values that were tied        18
Maximum difference allowed between ties 0.00001

Cases Included 59    Missing Cases 17

Statistix 9.1                                          5/17/2015, 2:37:57 PM

Wilcoxon Rank Sum Test for Rec3 VS Ini3

Variable    Rank Sum      N      U Stat    Mean Rank
Rec3         409.00       21     178.00       19.5
Ini3         1361.0       38     620.00       35.8
Total        1770.0       59

Normal Approximation with Corrections for Continuity and Ties    3.491
Two-tailed P-value for Normal Approximation                      0.0005

Total number of values that were tied        17
Maximum difference allowed between ties 0.00001

Cases Included 59    Missing Cases 17
```

FIG. 17

METHODS OF DIAGNOSING *CLOSTRIDIUM DIFFICILE* INFECTION OR RECURRENCE IN A SUBJECT

RELATED APPLICATION

This application is a non-provisional application claiming priority to U.S. Provisional Patent Application No. 62/433,870, filed Dec. 14, 2016, the entirety of which is incorporated herein.

BACKGROUND OF THE INVENTION

C. diff. infection (CDI) is an acute bacterial infection that affects the colonic epithelium and causes diarrhea. The infection has increased due to antibiotic overuse and development of an epidemic or more virulent strain. It currently is the largest nosocomial infection, costing the health care system between 1-3 billion dollars annually. Very little is known about how and what role the cellular immune response plays in clearance and/or recurrence of the infection.

Currently, confirming the presence of CDI in a patient relies on testing stool. In that regard, there are three main types of tests. The first and the oldest is the cell cytotoxicity assay. This requires a specific cell line and takes 24-48 hours to obtain results. This is not typically run in clinical labs. Secondly, the enzyme immunoassays ("EIA") can be used. These assays test for the presence of toxin A or B in the stool and are faster than the cell cytotoxicity assays. However, they are not as sensitive and are dependent on fresher stool and sampling. Up to 4 tests could be ordered over a 3-5 day period at some clinics.

A third test, PCR, has found clinical use. Although a bit more costly and more dependent on molecularly trained and knowledgeable staff, these tests are typically only ordered once every 7-14 days. They are less dependent on the freshness of stool as they measure the presence of bacterial toxin in DNA. Many of the common C. diff. strains produce both toxin A and toxin B—hence most new PCR or PCR-like tests (LAMP tests) amplify one or the other of the toxin genes in the pathogenic locus. The most widely used PCR test is for Toxin B. One example of a PCR test is Meridian's LAMP test, which amplifies a conserved DNA region of Toxin A gene within the PaLoc of C. diff. Testing by PCR, as well as the LAMP assay, demonstrates the presence of pathogenic bacteria but does not actually identify the toxin proteins. However, these toxin proteins are key to the pathogenic effects of inflammation and colonic epithelial destruction leading to the symptom of diarrhea. Toxins A & B have been shown to directly impact mitochondria and to affect apoptosis. Additionally, C. diff. Toxin A causes early damage to mitochondria in cultures cells.

Recently, a very rapid, albeit less sensitive test, entered the market. Known as the Alere Quik Chek® test (AQC), this test is highly dependent on the freshness of the stool. Using a colorimetric assay, AQC tests stool for the presence of glutamate dehydrogenase (GDH) antigen and toxins A & B. GDH is a metabolic enzyme produced by C. diff (toxigenic and non-toxigenic) as well as other bacteria. Hence for a verification of an infection caused by C. diff., both GDH and Toxin A/B portions of the assay must be positive.

Using a simple blood test to either verify or determine CDI may be useful, as there is always the "ick" factor to stool. Procuring stool is sometimes difficult, as patients may not be able to provide samples (after surgery and NPO), ostomy's provide problems of fresh stool, and from our experience, recurrent patients may or may not have truly watery stool, and therefore, some recurrence may be missed. Furthermore, the toxin or bacterial DNA may not be homogenously spread throughout a larger stool sample and therefore the threshold for PCR, ELISA, (EIA), and LAMP may be missed. Diarrhea is a primary symptom and the symptom that triggers the ordering of a CDI LAMP test. However, in some hospitals for every one positive CDI patient, 8-10 negative patients are tested. Before running a more costly CDI LAMP test, the blood test could be performed to determine if a LAMP test is warranted (i.e. the diarrhea is caused by C. diff. toxin exposure). This would be a costs savings for the health care system.

SUMMARY OF THE INVENTION

An aspect of the invention is directed toward a method of differentiating patients with *Clostridium difficile* (C. diff.) infection from those patients without C. diff. infection (CDI). The method includes obtaining a blood sample from a patient, such as a patient presenting with symptoms of CDI or suspected of having CDI. The blood sample is analyzed to provide a complete blood count. During this analysis, the different cell types, such as neutrophils, lymphocytes, monocytes, eosinophils, and early granulocytes, in the sample are resolved such as with a flow cytometer. Then, a value for a measurable property of one or more of the resolved cell types, such as axial light loss, is obtained for each of the cell types. This value is then compared to a pre-established threshold value, and the patient is diagnosed C. diff. infection if the value of the measurable property is above the pre-established threshold value. Embodiments of the method also include evaluating the additive effect of the measurable value for multiple cell types. Another aspect of the invention is directed to kits for practicing the method including the reagents necessary for the analysis. A further aspect of the invention is directed to initiating a therapeutic response, which may include administering a pharmaceutical agent to the subject, based on the results of the analysis.

A further aspect of the invention is directed toward methods of differentiation of patients who have, or will have, recurrent C. diff. infection. In an embodiment of this aspect of the invention, low angle light scatter analysis of circulating cell samples is used for this differentiation. During this analysis, the different cell types, such as neutrophils, lymphocytes, monocytes, eosinophils, and early granulocytes, in the sample are resolved such as with a Coulter counter. The method also includes evaluating the additive effect of the measurable value for multiple cell types. In another embodiment of this aspect of the invention, flow cytometry of peripheral blood samples is used for the differentiation by phenotyping the cells based on immunoglobulin response to bacterial toxins and surface antigens that characterize patients who will become recurrent. The patients may also be differentiated based on the ratio of lymphocytes to monocytes in the blood sample in accordance with this aspect of the invention. Another aspect of the invention is directed to kits for practicing the method including the reagents necessary for the analysis. A further aspect of the invention is directed to initiating a therapeutic response, which may include administering a pharmaceutical agent to the subject, based on the results of the analysis.

To be clear, the present application describes the technological process of diagnosing a C. Diff. infection in a subject and to differentiate subjects who have, or will have, recurrent C. Diff. infections. In accordance with this invention, this technological process is improved in any number of ways. For instance, an improvement is the non-invasive nature of the present invention is a blood test that does not require the collection of a stool sample. Moreover, in embodiments of the invention, the blood utilized for the test may be excess blood drawn from the subject for other medical testing and that would have otherwise been discarded without use. In other words, this invention allows the doctor to diagnose a C. Diff. infection in a subject and to differentiate subjects who have, or will have, recurrent C. Diff. infections by simply analyzing a blood sample. Another improvement is in the increased speed, accuracy, and reliability of a C. Diff. infection in a subject and to differentiate subjects who have, or will have, recurrent C. Diff. infections in accordance with this invention.

BRIEF DESCRIPTION OF THE DRAWINGS

FIG. 2 is a table of data collected in accordance with aspects of the invention.

FIG. 4 is a table of data collected in accordance with aspects of the invention.

FIG. 5 is a table of data collected in accordance with aspects of the invention.

FIG. 7 is a table of data collected in accordance with aspects of the invention.

FIG. 8 is a table of data collected in accordance with aspects of the invention.

FIG. 10 is a table of data collected in accordance with aspects of the invention.

FIG. 12 is a table of data collected in accordance with aspects of the invention.

FIG. 14 is a table of data collected in accordance with aspects of the invention.

FIG. 15 is a table of data collected in accordance with aspects of the invention.

FIG. 17 is a table of data collected in accordance with aspects of the invention.

DETAILED DESCRIPTION

Figure 1:
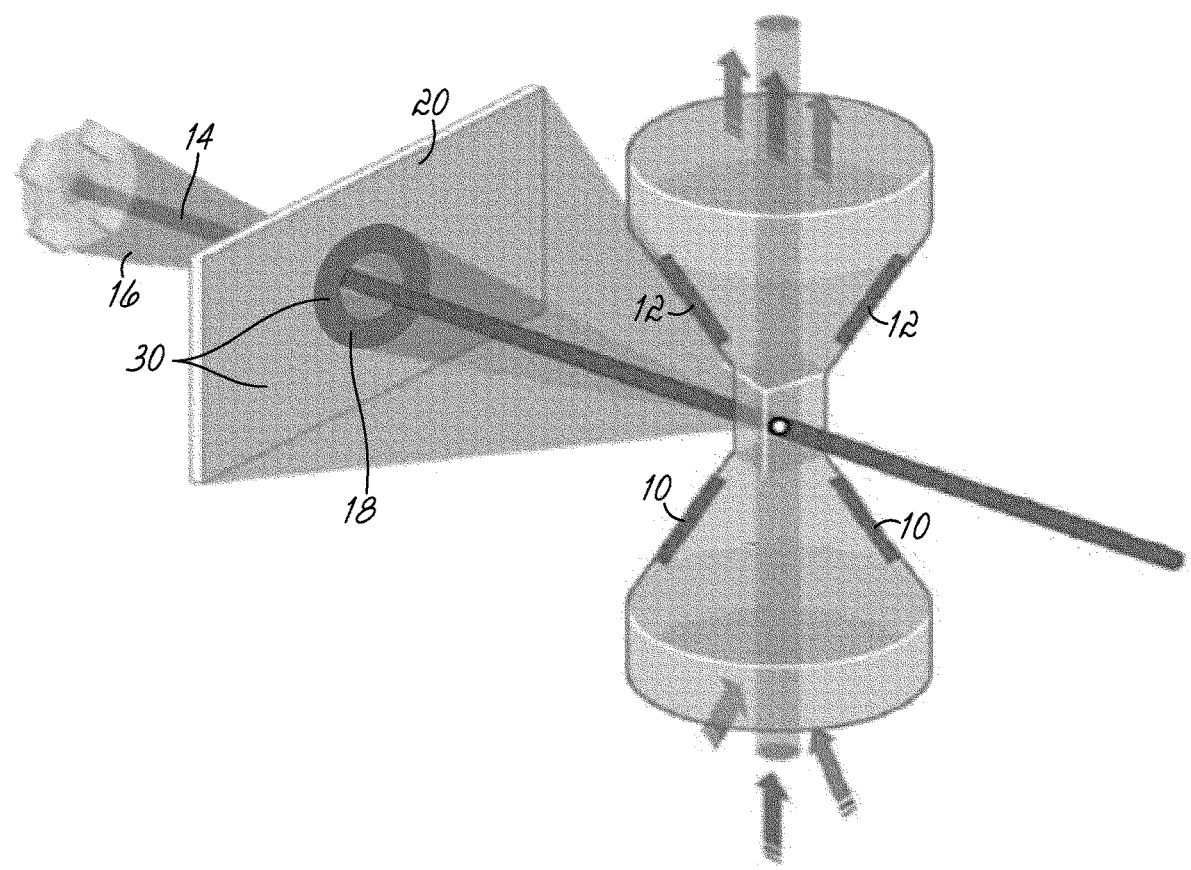
FIG. 1 is a schematic representation of the detectors in a Coulter counter.

An embodiment of the present invention allows stratification using a CBC of patients who are positive for C. diff. infection (CDI+) from CDI negative patients using a Coulter counter. FIG. 1 is a schematic diagram of the light angle collected using a Coulter system. The Coulter counter includes a lower electrode 10, an upper electrode 12, as well as detectors for axial light loss 14, low angle light scatter 16, lower median angle light scatter between 10 and 20 degrees (LMALS) 18, upper median angle light scatter between 20 and 42 degrees (UMALS) 20, and a fifth light scatter channel 30 that is the sum of the UMALS and the LMALS regions.

In accordance with aspects of this invention, the same tube of blood drawn for a standard of care CBC (complete blood count), which most hospital patients have drawn to assess their status in the hospital, may be used for sample analysis. Otherwise it is a simple blood draw such as collected in one purple 3 ml tube. For hospital patients, excess blood from standard of care CBC blood draws may be repurposed—thus, no extra blood draw is necessary.

Embodiments of the present CDI+ test, based on cellular immune response, are independent of measuring toxin from stool. This aspect of the invention includes a simple blood test to identify a change in the AL2 (axial light loss) that will verify that the blood cells have been exposed to a toxin. In embodiments, the patient may present with symptoms of C. diff. infection, such as diarrhea, prior to the blood sample being drawn. Without intending to be bound by any particular theory, the inventors hypothesize that AL2 changes are due to mitochondrial changes in response to toxin exposure.

In accordance with this aspect of the invention, the presence of toxin or C. diff. bacterial DNA is not measured. Instead, an effect of toxin on immune system cells in the blood is measured. Thus, a symptom or a reaction, like diarrhea or a higher white blood cell count is measured. Additionally, the AL2 effect is less pronounced in recurrent patients, most likely due to a changing or alternate cellular response, i.e. toxin is not the only component causing the immune response.

As discussed above, the acute infection of C. diff. is marked by a cellular response that can be defined by circulating cells that have a higher AL2 (axial light loss) or absorbed light relative to healthy controls. In an embodiment, the AL2 value for a patient with acute C. diff. infection is significantly elevated compared to uninfected controls. This value is then compared to a pre-established threshold value, and the patient is diagnosed C. diff. infection if the value of the measurable property is above the pre-established threshold value. In another embodiment, the threshold is an AL2 value that is elevated by at least 10% of the AL2 value from a population of uninfected controls. In an embodiment, the threshold is an AL2 value that is elevated by at least 15% of the AL2 value from a population of uninfected controls. In another embodiment, the threshold is an AL2 value that is elevated by at least 20% of the AL2 value from a population of uninfected controls. This difference can be detected in the circulating cells derived from a simple blood draw. The inventors theorize that the AL2 differences are due to cellular mitochondrial changes caused by exposure pf blood to toxin from the intestine. In practice, AL2 is determined for circulating cells from a patient's blood. In an embodiment, the circulating cells are neutrophil lymphocytes, monocytes, eosinophil, early granulocytes, or combinations thereof.

The AL2 demonstrates statistically different population demographic between CDI+ patients and those patients who test negative for CDI. Using cell population analysis of neutrophils, lymphocytes, monocytes, and eosinophils, significant differences, as shown below in Table 1 are demonstrated. The quantitative measurement reported by the Coulter counter is the mean channel (from 1-255) of the light scatter/loss in the AL2 channel collector. These mean numbers for each patient were recorded and compared using non-parametric analysis with Statistix 9 software.

TABLE 1

| Cell population | Kruskal-Wallis One way non-parametric anova | Comparison | Wilcoxan Rank Sum non-parametric statistic (p value) |
|---|---|---|---|
| Neutrophils | P = .0215 | | |
| | | CDI negative (Case) vs Initial CDI+ | .0011 |
| | | CDI negative (Case) vs Recurrent CDI+ | .0612 |
| Lymphocytes | P = .0654 | CDI negative (Case) vs Initial CDI+ | .0069 |
| | | CDI negative (Case) vs Recurrent CDI+ | .0431 |
| Monocytes | P = .1329 | CDI negative (Case) vs Initial CDI+ | .0066 |
| EGCs | P = .1990 | CDI negative (Case) vs Initial CDI+ | .0218 |

Figure 3:
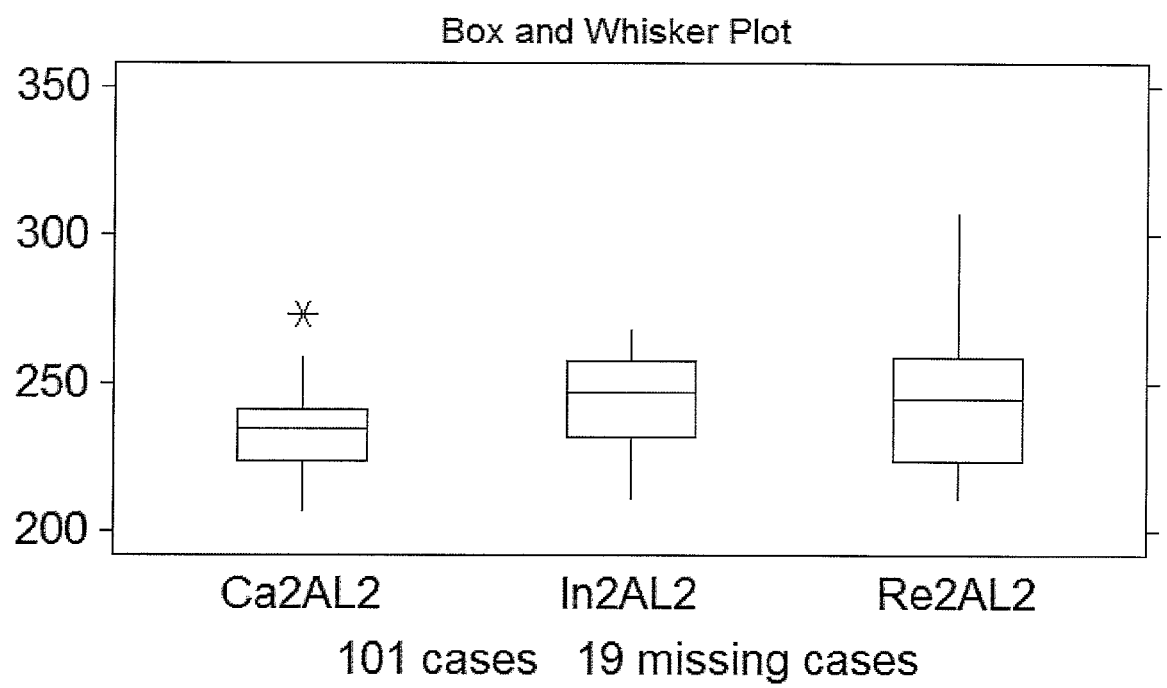
FIG. 3 is a plot of the data from FIG. 2.
Figure 6:
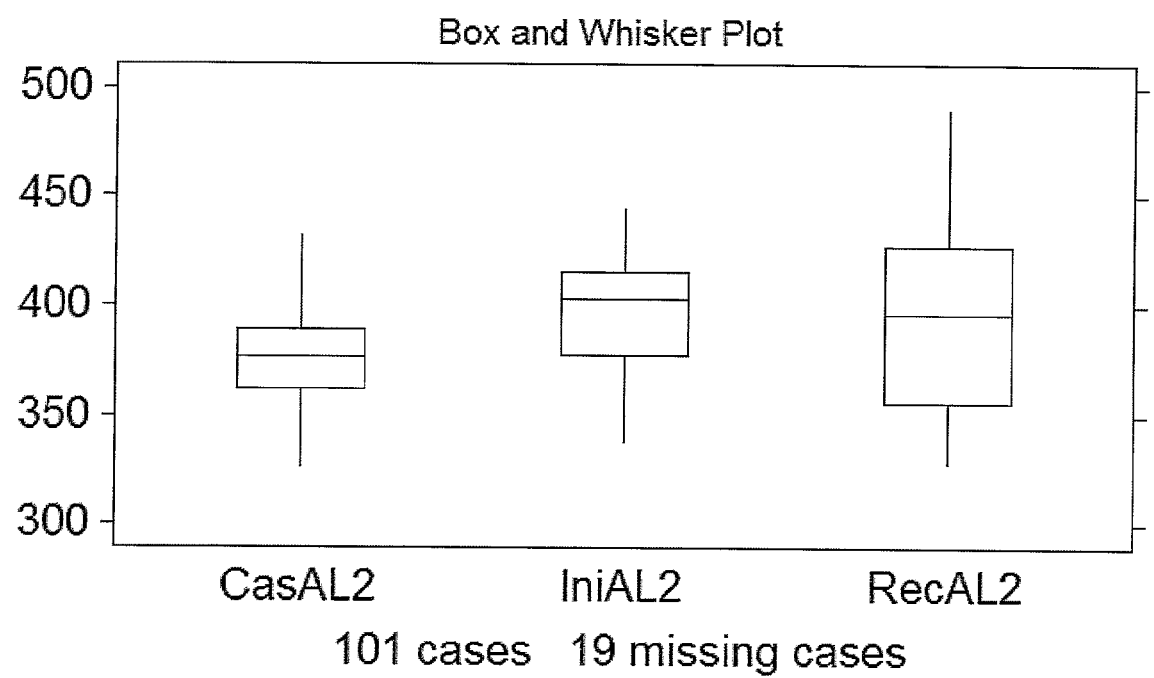
FIG. 6 is a plot of the data from FIG. 5.

If one combines the AL2 reported means from two cell types (neutrophils and lymphocytes) or three cell types (neutrophils+lymphocytes+monocytes), the differences relative to mean values from healthy controls become pronounced as shown in FIGS. 2-4. As shown in FIGS. 5-7, there appears to be a difference in the mono population in the recurrent CDI+ patients relative to the recurrent CDI trends, but this difference is not significant. One possibility is that AL2 depends on where in the course of treatment the recurrent infection is. Without being bound to a particular theory, AL2 may be linked to mitochondrial exposure to toxin presence and not likely from the inflammatory process left over after toxin production is shut down by treatment.

Figure 9:
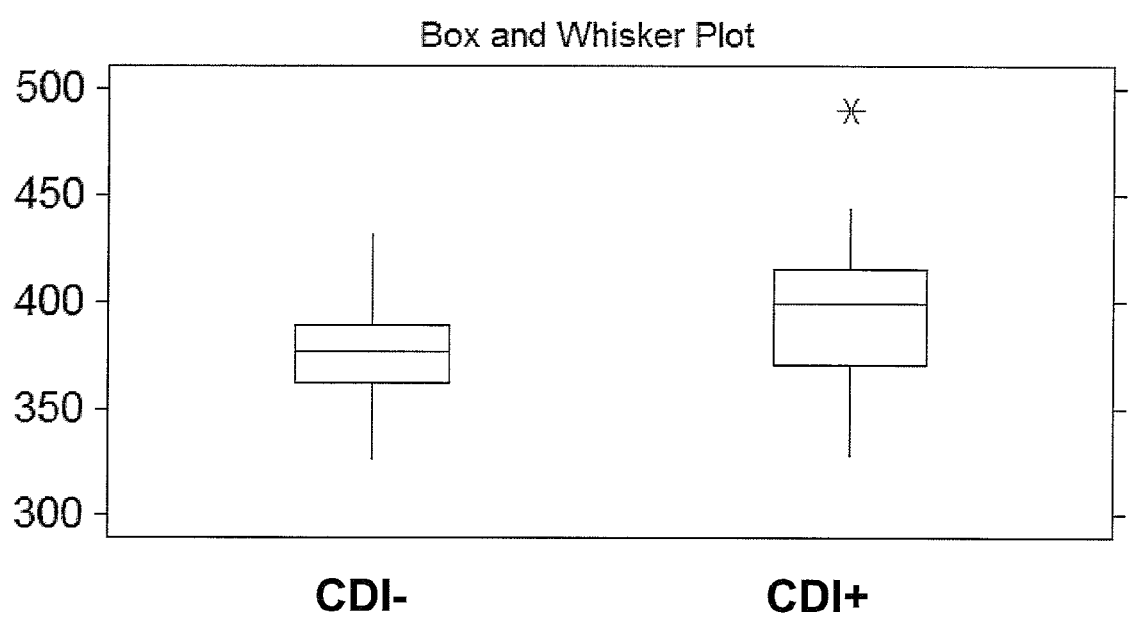
FIG. 9 is a plot of the data from FIG. 8.
Figure 11:
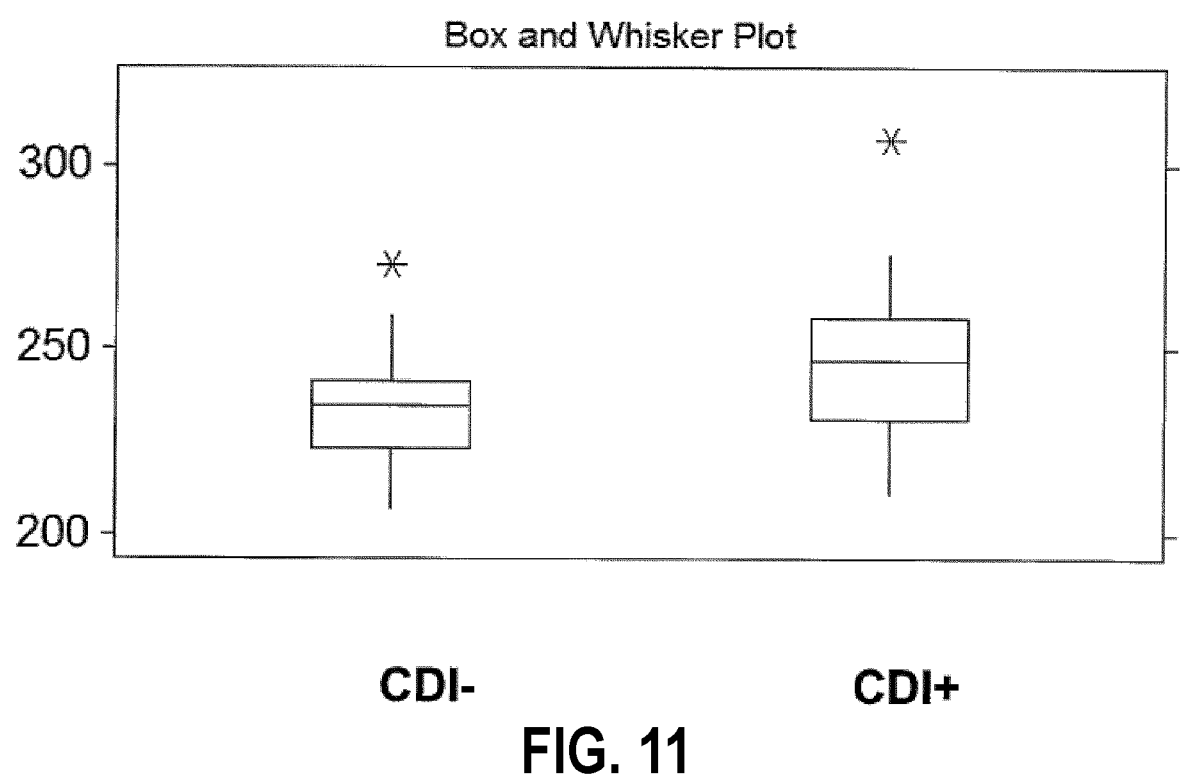
FIG. 11 is a plot of the data from FIG. 10.

FIGS. 8 and 9 show results when examining total CDI+ population (both recurrent and initial) vs. CDI negative populations when adding the three AL2 populations together (neutrophils+lymphocytes+monocytes). FIGS. 10 and 11 show results when examining total CDI+ population vs. CDI negative populations when adding two AL2 populations together (neutrophils+lymphocytes). In an embodiment, the AL2 value for a patient with acute C. diff. infection is significantly elevated compared to uninfected controls.

In another embodiment, the combined AL2 value is compared to a pre-established threshold value, and the patient is diagnosed C. diff. infection if the value of the measurable property is above the pre-established threshold value. In an embodiment, the threshold is an AL2 value that is elevated by at least 15% of the AL2 value from a population of uninfected controls. In another embodiment, the threshold is an AL2 value that is elevated by at least 20% of the AL2 value from a population of uninfected controls.

In another embodiment, the present invention allows stratification of patients who have, or will have, recurrent CDI using a CBC via a Coulter counter. Recurrent CDI, i.e. continued diarrheal symptoms after treatment with antibiotics, occurs in a large proportion of patients. At this time, all CDI patients are treated with primarily two antibiotics. Fifteen to thirty percent will fail the first course of antibiotics and continue to exhibit diarrheal symptoms again. The risk of further recurrence increases to 40-50% after first recurrence and then to 60-75% following the second recurrence.

Prior to this invention, there is no stratification of recurrent CDI in patients based on circulating cells. This aspect of the invention uses the CBC and population demographics that may be obtained using the Coulter counter. Using a Coulter counter, such as a UniCel DxH 800 Coulter Cellular Analysis System, the inventors have demonstrated a statistical difference in the population demographics between recurrent CDI+ and initial CDI+, i.e. those patients who clear the CDI after one standard of care therapy and case controls, i.e. those who have diarrhea and who test negative for CDI.

Using light angle scatter, the Coulter counter can measure and quantify the cells in a complete blood count (CBC). The typical CBC reported clinically includes a white blood cell count (WBC) as well as percent and absolute numbers of neutrophils, monocytes, lymphocytes, basophiles, and eosinophils, among other parameters. Some Coulter counters also report population demographics using different light scatter measurements. (V, C(SSC), MALS, LMALS, UMALS, LALS and AL2). Various cell populations may be identified by these light scatter measurements, such as neutrophils, lymphocytes, monocytes, eosinophils and early granulocytes (EGC's).

Without intending to be bound by any particular theory, recurrent CDI+ patients appear to respond differently to C. diff. infection. This difference may be detected in the circulating cells derived from a simple blood draw.

In this aspect of the invention, the lower angle light scatter (light scattered and collected between 0-5.1 degrees) (LAL) demonstrates statistically different population demographics between recurrent CDI, initial CDI, and case controls. Using single cell population analysis of neutrophils, monocytes and eosinophils, significant differences, as shown in Table 2, are demonstrated. The quantitative measurement reported by the Coulter counter is the mean channel (from 1-255) of the light scatter in the LALs channel collector. These mean numbers for each patient were recorded and compared using non-parametric analysis with Statistix 9 software.

TABLE 2

| Cell population | Kruskal-Wallis One way non-parametric anova | Comparison | Wilcoxan Rank Sum non-parametric statistic |
|---|---|---|---|
| Neutrophils | P = .0215 | | |
| | | Case vs Recurrent CDI | .0058 |
| | | Initial vs Recurrent CDI | .0606 |
| Monocytes | P = .0423 | Case vs Recurrent CDI | .0143 |
| | | Initial vs Recurrent CDI | .0317 |
| Eosinophils | P = .0484 | Case vs Initial | .0432 |
| | | Initial vs Recurrent | .0183 |

In an embodiment, the LAL value for a patient with recurrent C. diff. infection is significantly reduced compared to uninfected controls or patients with initial C. diff. infection. In another embodiment, the LAL value for a patient with acute C. diff. infection is reduced by at least 5% of the LAL value from a population of uninfected controls. In another embodiment, the LAL value for a patient with acute C. diff. infection is reduced by at least 10% of the AL2 value from a population of uninfected controls or patients with initial C. diff. infection. In another embodiment, the LAL value for a patient with acute C. diff. infection is reduced by at least 15% of the LAL value from a population of uninfected controls or patients with initial C. diff. infection.

Figure 13:
FIG. 13 is a plot of the data from FIG. 12.
Figure 16:
FIG. 16 is a plot of the data from FIG. 15.

If one combines the LALs reported means from two (neutrophils and monocytes) or three (neutrophils+monocytes+eosinophils), the differences become more pronounced, as shown in FIGS. 12-14. When adding the means of all three populations, not all patients had eosinophils in their blood. Hence, the n was smaller for each of the three patient groups, as shown in FIGS. 15-17.

In an embodiment, the LAL value from the combination of two or three cell types from a patient with recurrent C. diff. infection is significantly reduced compared to uninfected controls or patients with initial C. diff. infection. In another embodiment, the LAL value from the combination of two or three cell types from a patient with acute C. diff. infection is reduced by at least 5% of the LAL value from a population of uninfected controls. In another embodiment, the LAL value from the combination of two or three cell types from a patient with acute C. diff. infection is reduced by at least 10% of the AL2 value from a population of uninfected controls or patients with initial C. diff. infection. In another embodiment, the LAL value from the combination of two or three cell types from a patient with acute C. diff. infection is reduced by at least 15% of the LAL value from a population of uninfected controls or patients with initial C. diff. infection.

In yet another embodiment, the present invention utilizes peripheral blood and flow cytometry to stratify patients who will become recurrently C. diff. infected. The present invention makes it possible to identify those patients who will become recurrent at the point of their initial infection and therefore change their treatment strategy. The clinician may use a different antibiotic regimen (Fidaxomicin vs. Flagyl/Metronidazole or Vancomycin) or administer additional therapy that addresses the type of host's cellular response (possible anti-inflammatory agents). Additionally, as more community associated CDI occurs, knowing a potential outcome (clearance vs. recurrence) also helps contain the community spread of the infection. The stratification of patients who will become recurrently infected with C. diff. will impact hospital stay, hospital cost and community costs and spread. Currently, there are no methods or schemes of stratification of CDI patients, at any time during their infections.

The literature supports that those who become recurrent demonstrate a less efficient immunoglobulin response (detectable in serum) to bacterial toxins and surface antigens than those who do not become recurrent. There is currently no commercial test for the less efficient immunoglobulin response and it does not allow the stratification of the patients at the point of initial infection. An alternative study described how recurrence relates to inflammatory markers in the stool. But, once again, this is not commercially available and is not done at the time of initial infection.

To the inventors' knowledge, cellular differences in circulating PBMC in actual CDI patients have never been explored or exploited for the stratification of patients who will become recurrently infected with C. diff.

Figure 18A:
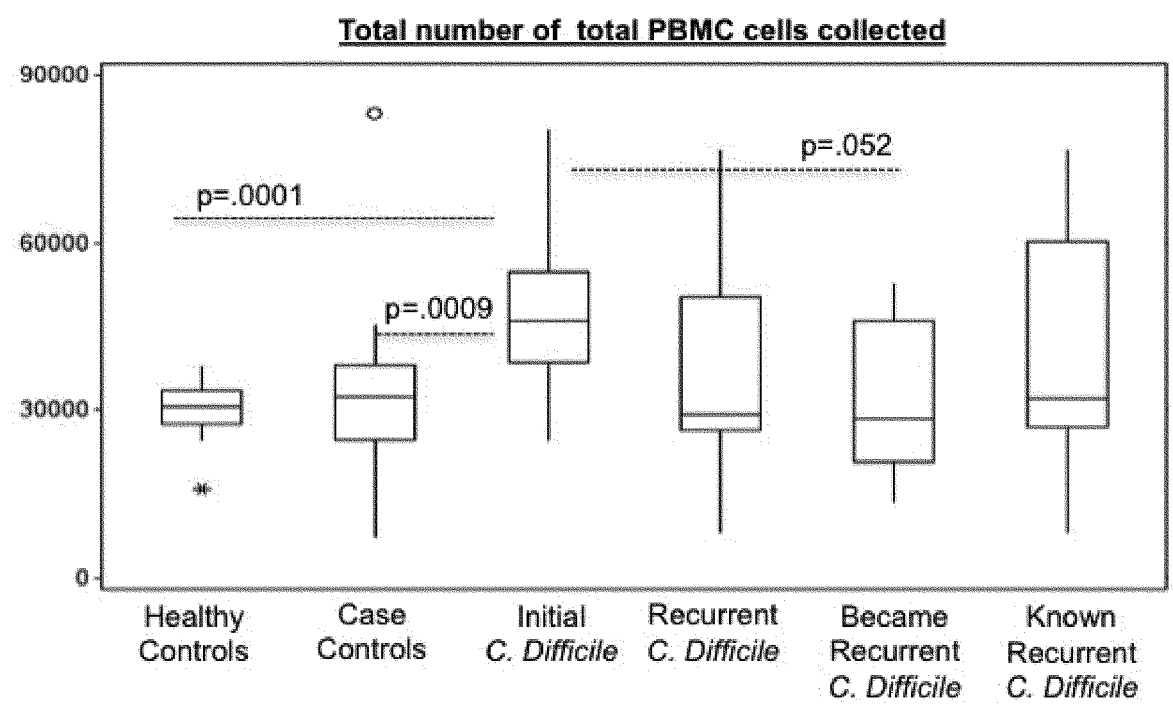
FIG. 18A is a plot of PMBC cells collected in samples from subjects in accordance with aspects of the invention.

Previous studies noted differences in T cell responses (plasticity and cytokine production) between recurrent CDI, initial CDI, and case control CDI patient groups. It was also noted that there were different types of circulating cells based on cell size (FSC) and granularity (SSC). For example, two times as many cells had to be collected from those patients who cleared their CDI in order to collect 20,000 events in the lymphocyte gate. In FIG. 18a, PBMC were isolated using ficoll density separation. Cells were stained with fluorescent markers to determine T cell phenotype. In accordance with aspects of this invention, the phenotyping can be done in most modern clinical labs, where flow cytometry has become integral in diagnostics.

Figure 18B:
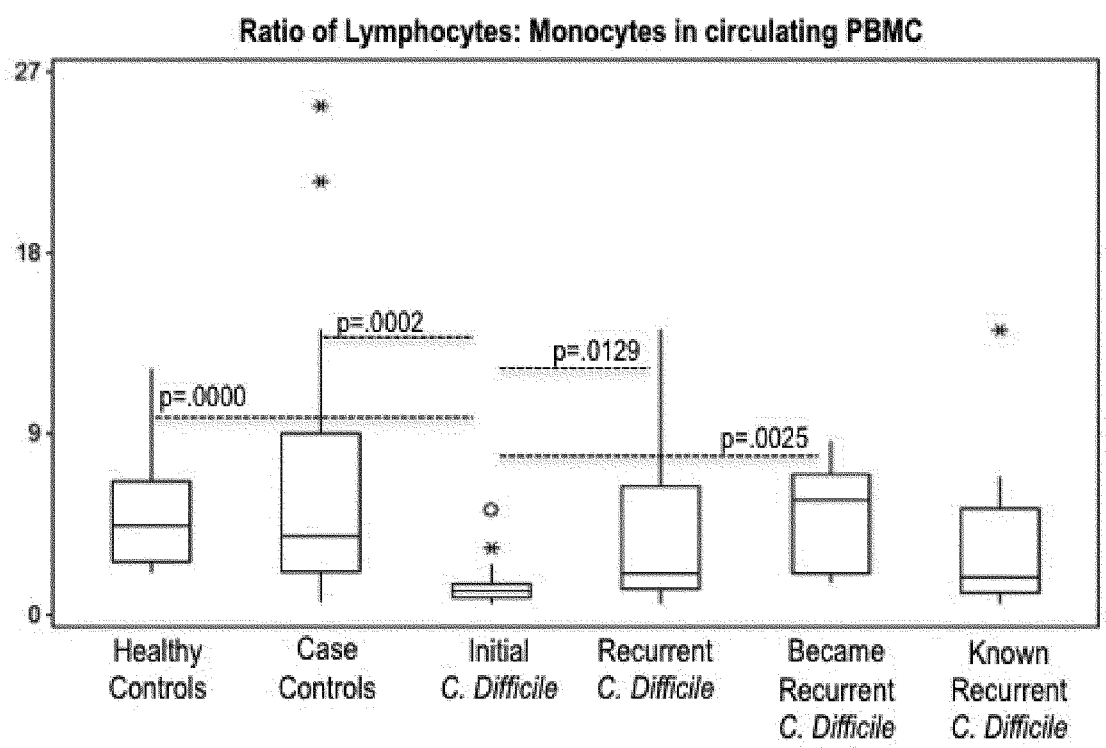
FIG. 18B is a plot of the ratio of lymphocytes to monocytes in sample from subjects in accordance with embodiments of the invention.

Using flow cytometry, cells were collected until 20,000 lymphotcyte events (based on size and granularity) were obtained. More cells needed to be collected in the Initial CDI group to reach 20,000 lymphocytes. As shown in FIG. 18b, once 20,000 lymphocytes were collected, the ratio of lymphocytes to monocytes was calculated.

In an aspect of the invention, the focus was on the types of T lymphocytes. We selected patients who would have T cells and thus excluded cancer, HIV, transplant, IBD, and any immunosuppressed patients. T cell plasticity and inflammatory T cells were investigated.

Figure 19:
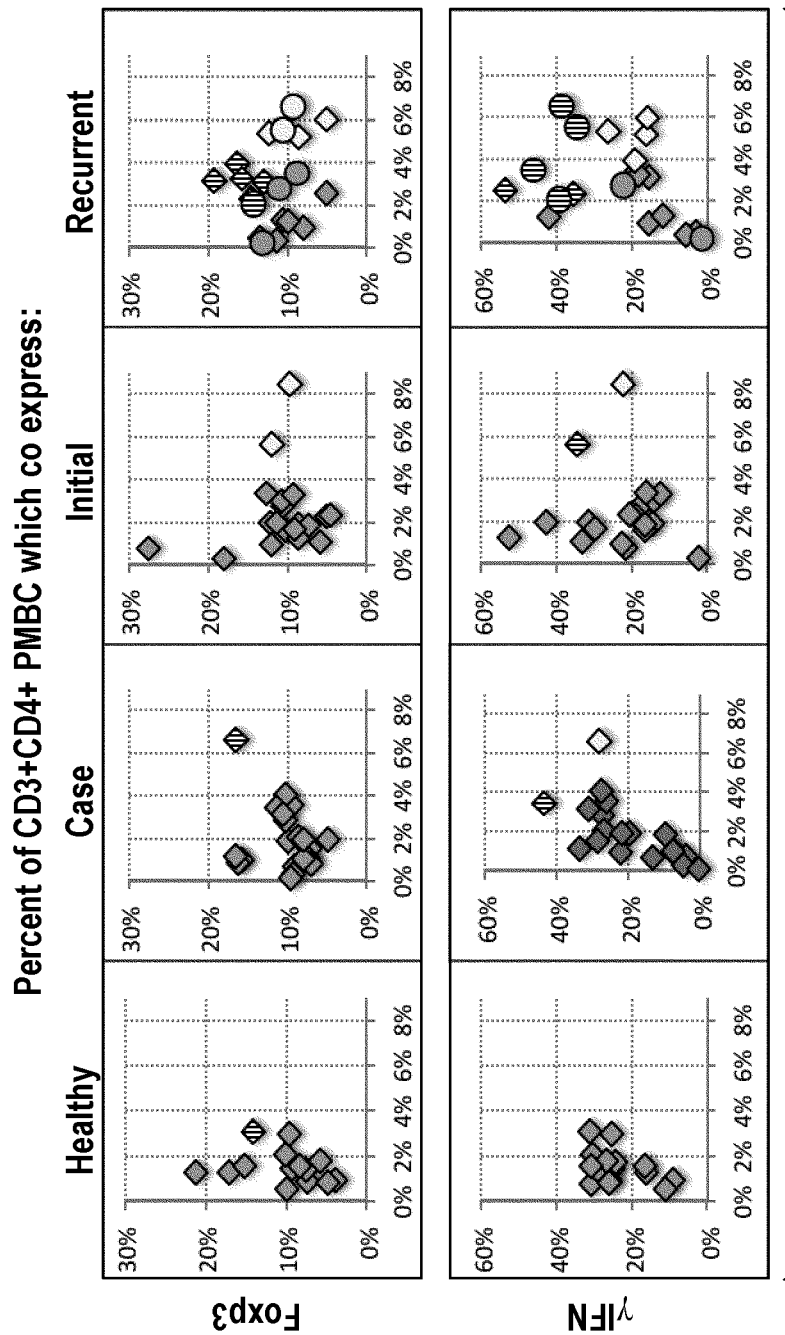
FIG. 19 is a plot of PMBC cells subtypes collected from subjects in accordance with embodiments of the invention.

As shown in FIG. 19, the percent of CD3+CD4+ cells which co-expressed IL17 and Foxp3 or γ-IFN was plotted in order to examine the pro-inflammatory or regulatory nature of the CD3+CD4+ population for reach individual case. Circles represent the 6 patients whose blood was taken at the time of primary CDI, but who later became recurrent. Striped circles or diamonds represent plasticity of co-expression and white diamonds or circles represent skewed IL17 co-expression. However, these data do not explain what causes the FSC/SSC population differences, which explanation would identify a key cellular difference in the recurrent CDI response. The phenotype of the potential cell type(s) has not been described or presented previously.

In an aspect of the invention, phenotypic differences based on fluorescent cell surface markers may be used for stratification of patients who become CDI. In embodiments of the invention, all patients, regardless of immune status, may be examined. Also, embodiments may not require ficoll purifying the peripheral blood mononuclear cell population and may analyze all white blood cell populations in the blood. In embodiment, at least 100,000 total cells are collected with no gate. In other embodiments, 20,000 cells are collected in the lymphocyte gate.

Trials used 3 patients selected at random; all three were diagnosed with CDI via the LAMP test. Of these three, one became recurrent. For the experiment, discarded clinical lab CBC was used and staining and flow cytometry was carried out in the clinical lab using their protocols. Such a regimen allows for the use of this work as a clinical test for stratifying CDI patients in order to determine the best therapeutic route to take. Using the discarded CBC, the inventors stained the cells for CD4, CD8, CD3 CD16 and CD56.

Single color histograms from the lymphocyte and monocot subset of cells were also generated. Whole blood was stained with the 5-antibody combination. All antibodies were directly fluorescently labeled. Using flow cytometry, 100,000 total cellular events were collected. Based on size (forward light scatter, FSC) and granularity (side light scatter, SSC) this sampling included lymphocyte, monocyte, and granulocyte populations. Table 3 provides the absolute number of lymphocytes and monocytes in each sample, along with the ratio of lymphocytes to monocytes. As can be seen in Table 3, the recurrent CDI patient exhibited a much higher ratio of lymphocytes to monocytes.

TABLE 3

| Patient | Total cells collected | Lymphocytes | Monocytes | Ratio of Lymphocytes: monocytes |
|---------|----------------------|-------------|-----------|--------------------------------|
| Cleared | 100,000 | 41692 | 9266 | 4.5 |
| Cleared | 100,000 | 14248 | 8022 | 1.78 |
| Recurrent | 100,000 | 22199 | 3121 | 10.64 |

Accordingly, in an embodiment of the invention, a subject is identified as being at risk of recurrent CDI if a blood sample from the patient exhibits an elevated ratio of lymphocytes to monocytes in a sample, when compared to a threshold value that may be based on data collected from either healthy controls or data collected from subjects who did not have recurrent CDI. In an embodiment, the threshold value is a ratio of lymphocytes to monocytes is at least 5:1. In another embodiment, the threshold value is a ratio of lymphocytes to monocytes is at least 8:1. In another embodiment, the threshold value is a ratio of lymphocytes to monocytes is at least 10:1.

While collecting data in support of this aspect of the invention, differences were observed in histogram profiles between the recurrent patients and patients who cleared CDI, suggesting that the phenotype, and therefore function of the immune response, could be different. Further differences can be demonstrated when two (FL2 vs. FL3 in all lymphocytes) or three (identified FL4 lymphocytes first then observed FL2 vs. FL3) populations are analyzed together.

A two-color analysis of the lymphocyte population, CD56 (FL2) vs. CD16 (FL3) demonstrated the distinct difference and presence of a CD3−CD56+CD16+ cell population in the recurrent CDI patient. The red population, which was present in the data collected from CD56 (FL2) vs. CD16 (FL3) lymphocyte population, and was absent in the data collected from the analysis of only the CD3+ lymphocyte population.

These differences will allow for stratification of patients who cannot clear CDI, relapse, or become CDI recurrent, and therefore, should be given alternative therapy. These phenotypic and composition differences also demonstrate how different immune responses in the intestine can be detected and studied in the circulating PBMC.

While the disclosed invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. The invention in its broader aspects is, therefore, not limited to the specific details, representative apparatus and method, and illustrative examples shown and described. Accordingly, departures may be made from such details without departing from the spirit or scope of the general inventive concept.

What is claimed is:

1. A method of differentiating patients with recurrent C. diff. infection from those patients with initial C. diff. infection comprising
    obtaining a blood sample from a patient;
    obtaining a glycoprotein stain by staining the blood sample for each of CD4, CD8, CD3, CD16, and CD56;
    phenotyping the blood sample based on the glycoprotein stain; and
    separating patients with recurrent C. diff. infection from those patients with initial C. diff. infection based on at least one of the phenotype of the blood sample or the ratio of lymphocytes to monocytes in the blood sample.

2. The method of claim 1 further comprising administering a pharmaceutical agent to the subject.

\* \* \* \* \*